United States Patent
Kim et al.

(10) Patent No.: US 9,562,227 B2
(45) Date of Patent: Feb. 7, 2017

(54) METHOD FOR SCREENING ANTICANCER AGENT OR SIP1/ZEB2 INHIBITOR USING INTEGRIN ALPHA 5

(75) Inventors: Semi Kim, Daejeon (KR); Hee Young Kang, Daejeon (KR); Myoung Suk Choi, Daejeon (KR); Mi-Ra Lee, Daejeon (KR); Jin-San Yoo, Daejeon (KR); Young Kyu Park, Gwangju (KR)

(73) Assignee: Korea Research Institute of Bioscience & Biotechnology, Daejeon (KR)

( * ) Notice: Subject to any disclaimer, the term of this patent is extended or adjusted under 35 U.S.C. 154(b) by 1181 days.

(21) Appl. No.: 13/500,502

(22) PCT Filed: Dec. 5, 2008

(86) PCT No.: PCT/KR2008/007209
§ 371 (c)(1),
(2), (4) Date: Apr. 5, 2012

(87) PCT Pub. No.: WO2010/061997
PCT Pub. Date: Jun. 3, 2010

(65) Prior Publication Data
US 2012/0201838 A1    Aug. 9, 2012

(30) Foreign Application Priority Data
Nov. 28, 2008  (KR) .................. 10-2008-0119773

(51) Int. Cl.
*C12N 15/113* (2010.01)
*G01N 33/50* (2006.01)

(52) U.S. Cl.
CPC ......... *C12N 15/113* (2013.01); *G01N 33/5011* (2013.01); *C12N 2310/14* (2013.01); *C12N 2320/12* (2013.01); *G01N 2333/7055* (2013.01)

(58) Field of Classification Search
None
See application file for complete search history.

(56) References Cited

U.S. PATENT DOCUMENTS

2006/0234259 A1   10/2006  Rubin et al.
2007/0128639 A1*   6/2007  Chinnaiyan et al. ............. 435/6
2008/0167532 A1    7/2008  Smallridge et al.

OTHER PUBLICATIONS

Vandewalle et al., Nucleic Acids Research, 2005, vol. 33, pp. 6566-6578.*
Vandewalle et al., Nucliec Acids Research, 2005, vol. 33, pp. 6566-6578.*
Anne Maglott, et al., "The Small alpha5beta1 Integrin Antagonist, SJ749, Reduces Proliferation and Clonogenicity of Human Astrocytoma Cells", Cancer Res, 66:(12), Jun. 15, 2006, pp. 6002-6007.
Sumito Koshida, et al., "Integrin alpha 5-Dependent Fibronectin Accumulation for Maintenance of Somite Boundaries in Zebrafish Embryos", Developmental Cell, vol. 8, Apr. 2005, pp. 587-598.

* cited by examiner

*Primary Examiner* — Mindy G Brown
(74) *Attorney, Agent, or Firm* — Lathrop & Gage LLP; Brian C. Trinque; Andrew T. Wilkins (57) ABSTRACT

The present invention relates to a method for screening anticancer agent or SIP1/ZEB2 inhibitor using integrin alpha 5 (ITGA5), more precisely a method for measuring integrin alpha 5 expression pattern in SIP1/ZEB2 over-expressing cell line or SIP1/ZEB2 expression induced cell line, both treated with sample compounds, by comparing with that of the control. The method of the present invention facilitates screening of anticancer agent or SIP1/ZEB2 inhibitor simply by measuring integrin alpha 5 expression, so that it can be effectively applied in the field of medicine.

6 Claims, 10 Drawing Sheets

ZEB2

ITGA5

E-cadherin

β-actin p-ERK

ERK

P-FAK(Y925)

P-FAK(Y397)

FAK

Fig. 10

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: SIP1/ZEB2 specific siRNA(sense)

<400> SEQUENCE: 1
gaacagacag gcuuacuuau u                                              21

<210> SEQ ID NO 2
<211> LENGTH: 21
<212> TYPE: RNA
<213> ORGANISM: Artificial Sequence
<220> FEATURE:
<223> OTHER INFORMATION: SIP1/ZEB2 specific siRNA(antisense)

<400> SEQUENCE: 2
uaaguaagcc ugucuguucu u                                              21

<210> SEQ ID NO 3
<211> LENGTH: 21
<212> TYPE: RNA
<213> ORGANISM: Artificial Sequence
<220> FEATURE:
<223> OTHER INFORMATION: SIP1/ZEB2 specific siRNA(sense)

<400> SEQUENCE: 3
gaagcuacgu acuuuaauau u                                              21

<210> SEQ ID NO 4
<211> LENGTH: 21
<212> TYPE: RNA
<213> ORGANISM: Artificial Sequence
<220> FEATURE:
<223> OTHER INFORMATION: SIP1/ZEB2 specific siRNA(antisense)

<400> SEQUENCE: 4
uauuaaagua cguagcuucu u                                              21

<210> SEQ ID NO 5
<211> LENGTH: 21
<212> TYPE: RNA
<213> ORGANISM: Artificial Sequence
<220> FEATURE:
<223> OTHER INFORMATION: SIP1/ZEB2 specific siRNA(sense)

<400> SEQUENCE: 5
caacauaucc acuccauuuu u                                              21

<210> SEQ ID NO 6
<211> LENGTH: 21
<212> TYPE: RNA
<213> ORGANISM: Artificial Sequence
<220> FEATURE:
```

<223> OTHER INFORMATION: SIP1/ZEB2 specific siRNA(antisense)

<400> SEQUENCE: 6 aauggagug gauauguugu u                                    21

<210> SEQ ID NO 7
<211> LENGTH: 21
<212> TYPE: RNA
<213> ORGANISM: Artificial Sequence
<220> FEATURE:
<223> OTHER INFORMATION: SIP1/ZEB2 specific siRNA(sense)

<400> SEQUENCE: 7
ggagacagau caguaauauu u                                   21

<210> SEQ ID NO 8
<211> LENGTH: 21
<212> TYPE: RNA
<213> ORGANISM: Artificial Sequence
<220> FEATURE:
<223> OTHER INFORMATION: SIP1/ZEB2 specific siRNA(antisense)

<400> SEQUENCE: 8
auauuacuga ucugucuccu u                                   21

<210> SEQ ID NO 9
<211> LENGTH: 20
<212> TYPE: DNA
<213> ORGANISM: Artificial Sequence
<220> FEATURE:
<223> OTHER INFORMATION: SIP1/ZEB2 specific primer(forward)

<400> SEQUENCE: 9
tctcgcccga gtgaagcctt                                     20

<210> SEQ ID NO 10
<211> LENGTH: 21
<212> TYPE: DNA
<213> ORGANISM: Artificial Sequence
<220> FEATURE:
<223> OTHER INFORMATION: SIP1/ZEB2 specific primer(reverse)

<400> SEQUENCE: 10
gggagaattg cttgatggag c                                   21

<210> SEQ ID NO 11
<211> LENGTH: 21
<212> TYPE: DNA
<213> ORGANISM: Artificial Sequence
<220> FEATURE:
<223> OTHER INFORMATION: beta-actin specific primer(forward)

<400> SEQUENCE: 11
gctcgtcgtc gacaacggct c                                   21

<210> SEQ ID NO 12
<211> LENGTH: 25
<212> TYPE: DNA
<213> ORGANISM: Artificial Sequence
<220> FEATURE:
<223> OTHER INFORMATION: beta-actin specific primer(reverse)

<400> SEQUENCE: 12
caaacatgat ctgggtcatc ttctc                               25

```
<210> SEQ ID NO 13
<211> LENGTH: 58
<212> TYPE: DNA
<213> ORGANISM: Artificial Sequence
<220> FEATURE:
<223> OTHER INFORMATION: SIP1/ZEB2 specific primer(forward)

<400> SEQUENCE: 13
gctctagaga gcagaaactc atctctgaag aggatctgat gaagcagccg atcatggc        58

<210> SEQ ID NO 14
<211> LENGTH: 28
<212> TYPE: DNA
<213> ORGANISM: Artificial Sequence
<220> FEATURE:
<223> OTHER INFORMATION: SIP1/ZEB2 specific primer(reverse)

<400> SEQUENCE: 14
gctctagatt acatgccatc ttccatat                                          28

<210> SEQ ID NO 15
<211> LENGTH: 27
<212> TYPE: DNA
<213> ORGANISM: Artificial Sequence
<220> FEATURE:
<223> OTHER INFORMATION: integrin alpha specific primer(forward)

<400> SEQUENCE: 15
gctctagaat ggggagccgg acgccag                                           27

<210> SEQ ID NO 16
<211> LENGTH: 26
<212> TYPE: DNA
<213> ORGANISM: Artificial Sequence
<220> FEATURE:
<223> OTHER INFORMATION: integrin alpha specific primer(reverse)

<400> SEQUENCE: 16
gctctagatc aggcatcaga ggtggc                                            26
```

METHOD FOR SCREENING ANTICANCER AGENT OR SIP1/ZEB2 INHIBITOR USING INTEGRIN ALPHA 5

CROSS-REFERENCE TO RELATED APPLICATIONS

This application is a 371 of PCT/KR2008/007209, filed Dec. 5, 2008, which claims the benefit of Korean Patent Application No. 10-2008-0119773, filed Nov. 28, 2008, the contents of each of which are incorporated herein by reference.

TECHNICAL FIELD

The present invention relates to a method for screening anticancer agent or SIP1/ZEB2 inhibitor using integrin alpha 5 (ITGA5), more precisely a method for screening anticancer agent or SIP1/ZEB2 inhibitor based on the examination of integrin alpha 5 expression pattern in SIP1/ZEB2 over-expressing cell line or SIP1/ZEB2 expression induced cell line.

BACKGROUND ART

Studies on cancer have been intensively going on for more than 30 years. Nevertheless, incidence rate of cancer is still increasing and environmental pollution and unbalanced diet habit might be a reason. Every year, 10 million cancer patients are newly reported world-widely. WHO recognizes cancer the leading cause of death.

Even if new treatment methods for cancer have been developed, surgical operation, radio-therapy and chemo-therapy are still co-treated largely. Generally, anticancer agent targets a specific cancer and does not have any effect on any other cancers. Besides, such anticancer agent can cause resistance. So, to increase effectiveness of cancer treatment, diverse novel anticancer agents have to be developed and a simple and easy screening method for them is also required.

While screening a target for a novel anticancer agent, the present inventors disclosed that invasion ability was increased in TMPRSS4 (transmembrane protease, serine 4) over-expressing cell line and when TMPRSS4 was inhibited by TMPRSS4 specific siRNA (small interfering RNA), invasion ability was reduced, suggesting that TMPRSS4 could be a target for the development of anticancer agent (Jung et al., Oncogene, 27: 2645-2647, 2008, Korean Patent Publication No 2007-0114970). The present inventors also confirmed in previous study that various factors were over-expressed when TMPRSS4 was over-expressed. Among those factors, the present inventors have focused on functions and roles of SIP1/ZEB2 and integrin alpha 5 (ITGA5).

SIP1/ZEB2 (Smad-interacting protein-1/Zinc finger E-box binding homeobox 2) is one of δEF-1 family which is two-handed Zinc finger nuclear factor. It is involved in epithelial mesenchymal transition (EMT) during developmental process. The mechanism is presumably as follows. SIP1/ZEB2 down-regulates the gene encoding a protein composing Gap-junction such as E-cadherin or desmosome (Vandevalle et al, Nucleic Acids Res. 33(20): 6566-6578, 2005). Besides, SIP1/ZEB2 accelerates cancer metastasis, in which double-negative feedback loop between SIP1/ZEB2 and microRNA-200 family is involved (Bracken et al., Cancer Res. 68(19):7846-54, 2008).

SIP1/ZEB2 and ZEB1, two members of δEF-1 family, have two zinc finger clusters. Each zinc finger cluster binds to E box (ex: CACCT). It was also confirmed by EMSA (electrophoretic mobility shift assay) that SIP1/ZEB2 binds to promoters of Xbra (Xenopus Brachyury), human integrin alpha 4 and human E-cadherin (Remacle et al., EMBO J. 18, 5073-5084, 1999). It is further known that SIP1/ZEB2 and ZEB1 are expressed in normal E-cadherin-negative tissues such as muscle cells and hematopoietic cells (Postigo and Dean, Proc. Natl. Acad. Sci. USA 97, 6391-6396, 2000). In particular, SIP1/ZEB2 binds to E-cadherin gene promoter to inhibit transcription of E-cadherin which is cell-cell adhesion molecule suppressing invasion, and accordingly cancer cell invasion is induced (Comijin et al., Mol. Cell 7: 1267-1278, 2001). In addition to SIP1/ZEB2, SNAI1 (snail homolog 1), SNAI2, TWIST and E47 are known as factors inducing cancer cell invasion and metastasis by suppressing E-cadherin transcription and inducing EMT (Peinado et al., Nature Rev. Cancer 7: 415-428, 2007). Those factors demonstrate different expression patterns according to the kind of cancer (Peinado et al., Nature Rev. Cancer 7: 415-428, 2007). SIP1/ZEB2 is largely expressed in ovarian cancer, stomach cancer, pancreatic cancer and squamous cell carcinoma (SCC), and ZEB1 is expressed in colon cancer and uterine cancer. TWIST and SNAI1 are up-regulated in diffuse subtype of stomach cancer, while SIP1/ZEB2 are up-regulated in intestinal subtype of stomach cancer (Rosivatz et al., Am. J. Pathol. 161: 1881-1891, 2002). The above results indicate that EMT and transition inducing factors make different combinations according to the type of cancer and thus play different roles. However, expression and functions of SIP1/ZEB2 in colon cancer have not been disclosed, yet.

ITGA5 (integrin subunit alpha5) is one of integrin subunits. Integrins are heterodimers comprising alpha and beta chains. After translation in extracellular domain, it forms light and heavy chains linked by disulfide bond and then binds to beta 1 to form a fibronectin receptor. Integrin family contains at least 25 combinations made by pairing of 18 alpha chains and 8 beta chains (van der Flier and Sonnenberg, Cell Tissue Res. 305:285-298, 2001). Integrin is a receptor mainly binding to extracellular matrix and is connected to intracellular actin cytoskeleton. Integrin is also known to be involved in cell-surface mediated signal transduction. Integrin alpha 5 beta 1 binds to fibronectin. Integrin alpha 5 is involved in progress, invasion and metastasis of liver cancer (Yao et al., Zhonghua Yi Xue Za Zhi. 77(5): 382-384, 1997) and melanoma (Mortarini et al., Cancer Res. 52(16):4499-4506, 1992). Integrin alpha 5 beta 1 is highly expressed rather in strong carcinogenic colon cancer cell line than in weak carcinogenic colon cancer cell line (Gong et al., Cell Growth & Differentiation 8:83-90, 1997). In the meantime, integrin alpha 5 beta 1 expression is almost inhibited during colon cancer development and when integrin alpha 5 beta1 is re-expressed in the colon cancer cell line originally not-expressing integrin alpha 5 beta1, HER-2 is down-regulated by integrin alpha 5 beta1, suggesting that integrin alpha 5 beta 1 (that is integrin alpha 5) has tumor suppressor-like activity (Kuwada and Li, Mol. Biol. Cell 11:2485-2496, 2000; Kuwada et al., J. Biol. Chem. 280: 19027-19035, 2005). However, it is still unknown what kind of role integrin alpha 5 (ITGA5) plays in colon cancer.

While screening a target material for screening anticancer agent or SIP1/ZEB2 inhibitor, the present inventors confirmed that cancer cell invasion was increased by SIP1/ZEB2 and integrin alpha 5 and when SIP1/ZEB2 was over-expressed, integrin alpha 5 was up-regulated. And further the present inventors completed this invention by developing a method for screening anticancer agent or SIP1/ZEB2 inhibitor using the said integrin alpha 5.

DISCLOSURE

Technical Problem

It is an object of the present invention to provide a method for screening anticancer agent or SIP1/ZEB2 inhibitor using integrin alpha 5 playing an important role in cancer cell invasion.

Technical Solution

To achieve the above object, the present invention provides a method for screening anticancer agent or SIP1/ZEB2 inhibitor containing the steps of treating sample compounds to SIP1/ZEB2 over-expressing cell line or SIP1/ZEB2 expression induced cell line and measuring integrin alpha 5 expression in the cell line.

Advantageous Effect

The present invention relates to a method for screening anticancer agent or SIP1/ZEB2 inhibitor using integrin alpha 5 (ITGA5) and thus can be applied in the field of medicine by simply screening anticancer agent or SIP1/ZEB2 inhibitor by measuring integrin alpha 5.

DESCRIPTION OF DRAWINGS

The application of the preferred embodiments of the present invention is best understood with reference to the accompanying drawings, wherein.

BEST MODE

Hereinafter, the present invention is described in detail.

The present invention provides a method for screening anticancer agent comprising the following steps:

step 1: transforming a cell line with SIP1/ZEB2 expression vector;

step 2: treating sample compounds to the cell line transfected above; and step 3: investigating whether the expression of integrin alpha 5 (ITGA5) in the cell line is reduced or not, compared with that in the control.

In step 1 of the screening method of the present invention, a cell line was transformed with SIP1/ZEB2 expression vector. The 'expression vector' herein is the vector capable of expressing a target protein or a target RNA in a proper host cell, which is linear or circular DNA molecule composed of fragments encoding polypeptide in interest operably linked to additional fragment provided for transcription. The additional fragment contains a promoter sequence and stop codon sequence. The expression vector contains one or more replication origins, one or more selection markers, and polyadenylation signal. The SIP1/ZEB2 expression vector of the present invention contains polynucleotide encoding SIP1/ZEB2 of fragments thereof. The expression vector is not limited to specific one but is properly selected considering environmental conditions such as transformation period and type, etc. The said vector can be delivered to the nucleus of a cell as pure plasmid DNA or as a complex formed with transformation reagent or target-delivering material or as a recombinant virus vector. For the virus vector, adenovirus, adeno-associated virus, and retrovirus including lentivirus, etc can be used.

The said expression vector is introduced in normal cells or cancer cells. At this time, any transformation method known to those in the art can be used. The cancer cell line herein is not limited but colon cancer cell line is preferred.

In a preferred embodiment of the present invention, myc-tag was added to N-terminal of cDNA encoding the full length of SIP1/ZEB2, followed by PCR for amplification. The PCR product was inserted into pcDNA3.1 (Invitrogen) to construct pcDNA3.1-myc-SIP1/ZEB2 expression vector. SW480 (colon cancer cell line) was transformed with the said expression vector. TMPRSS4, one of upstream targets inducing SIP1/ZEB2 expression, was also introduced in SW480 to construct transformed cell line.

In step 2 of the screening method of the present invention, the cell line transformed to over-express SIP1/ZEB2 was treated with sample compounds. The sample compounds herein are anticancer agent candidates, and preferably the candidates whose anticancer activities have not been known are preferred. Those sample compounds are preferably chemical compounds but not limited thereto and antisense nucleotide complementary to integrin alpha 5, siRNA (small interfering RNA), matrix analogue binding to integrin alpha 5, antibody, small compound inhibiting integrin alpha 5 activity, SIP1/ZEB2 inhibitor and its upstream target protein inhibitor can also be included. For the treatment, the sample compounds are added to the culture media at a specific concentration, or the sample compounds added to the cell lines, but not always limited thereto and any method known to those in the art can be used.

In step 3 of the screening method of the present invention, expression of integrin alpha 5 (ITGA5) was compared between the cell line treated with the sample compounds of step 2 and the cell line not-treated.

In a preferred embodiment of the present invention, when SIP1/ZEB2 was inserted in the cell line, integrin alpha 5 was up-regulated and the increased integrin alpha 5 induced colon cancer invasion (see Examples 1-4). So, integrin alpha 5 expression inhibitor is expected to have anticancer activity.

Expression pattern was examined by RT (reverse transcriptase)-PCR or Western blotting, but not always limited thereto and any method known to those in the art can be used.

Figure 1:
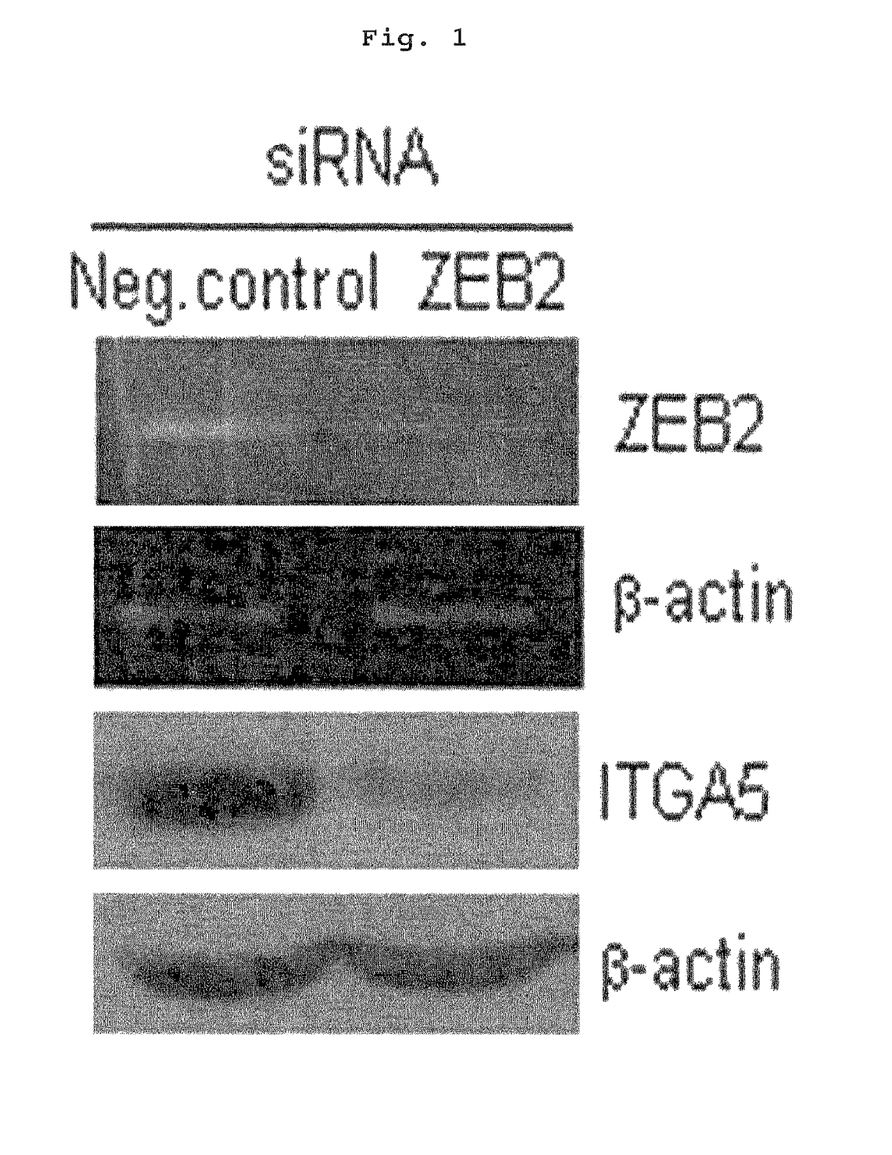
FIG. 1 is a diagram illustrating the results of RT-PCR and Western blotting measuring the levels of integrin alpha 5, SIP1/ZEB2 and β-actin (control) after inhibiting the expression of SIP1/ZEB2 using SIP1/ZEB2 specific siRNA.
Figure 2:
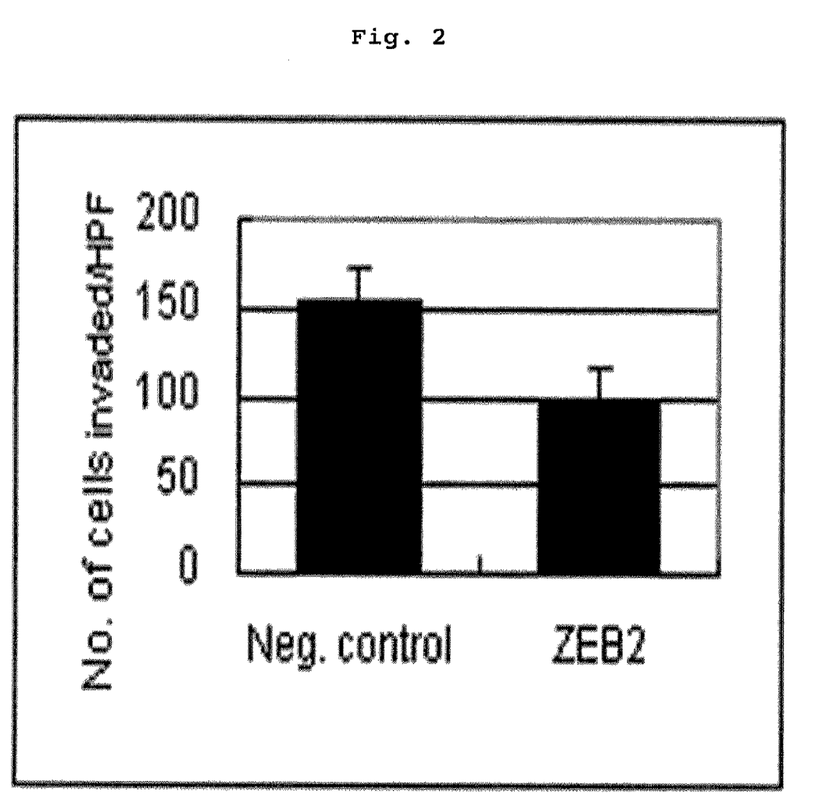
FIG. 2 is a graph illustrating the change of invaded cell number after inhibiting the expression of SIP1/ZEB2 using SIP1/ZEB2 specific siRNA.

To investigate the effect of SIP1/ZEB2 inhibition, SIP1/ZEB2 mRNA specific siRNA was inserted in the cell line in which SIP1/ZEB2 expression was induced by an upstream target (e.g. TMPRSS4). As a result, SIP1/ZEB2 expression was significantly reduced by siRNA and integrin alpha 5 (ITGA5) expression was also significantly reduced (FIG. 1). Invasion was also investigated. As a result, when siRNA was introduced, invasion capacity was reduced, compared with the control group (FIG. 2).

Figure 3:
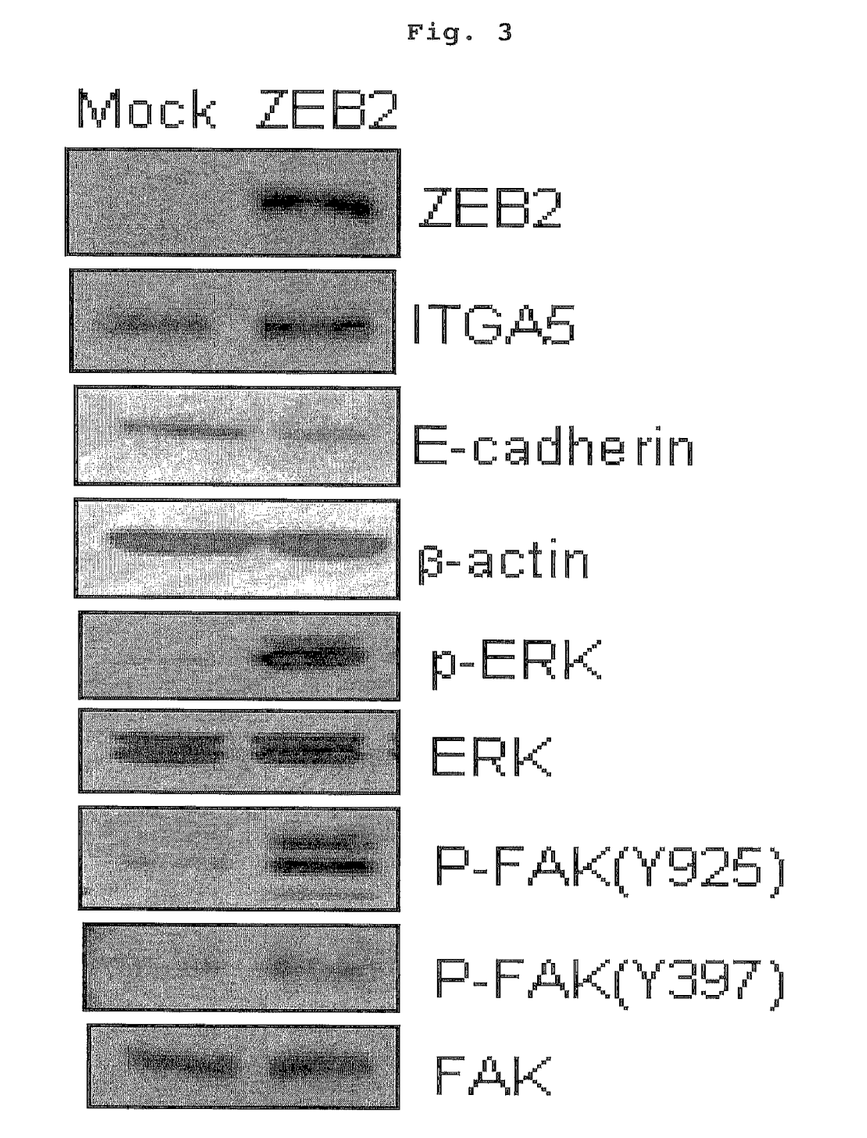
FIG. 3 is a diagram illustrating the results of Western blotting measuring the change of cell signal transduction and the expression levels of integrin alpha 5, E-cadherin and β-actin (control) after the insertion of SIP1/ZEB2.
Figure 4:
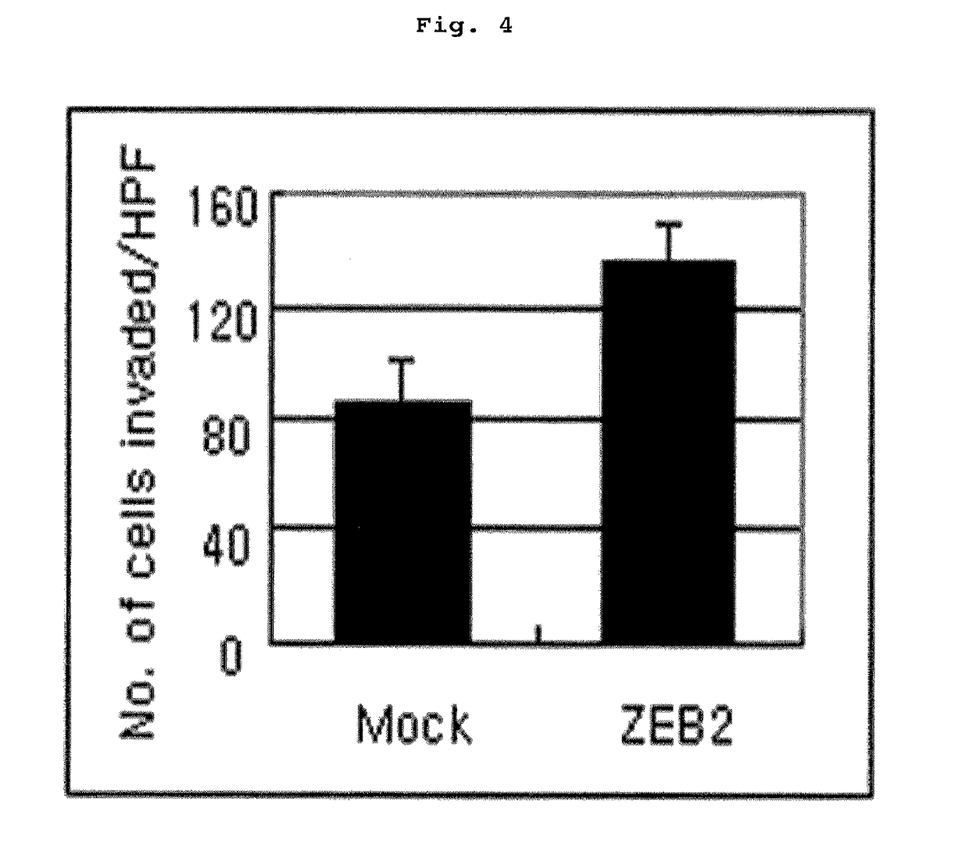
FIG. 4 is a graph illustrating the change of invaded cell number after the insertion of SIP1/ZEB2.

The effect of SIP1/ZEB2 introduction was further investigated. First, SIP1/ZEB2 was introduced into the cell line which does not over-express SIP1/ZEB2. As a result, SIP1/ZEB2 expression was increased and so was integrin alpha 5 expression (FIG. 3). Invasion of cancer cells was also increased in the cell line, compared with the control group (FIG. 4).

The results shown in FIG. 1-FIG. 4 indicate that SIP1/ZEB2 is involved in cancer cell invasion and metastasis and SIP1/ZEB2 induces integrin alpha 5 (ITGA5) expression.

Figure 5:
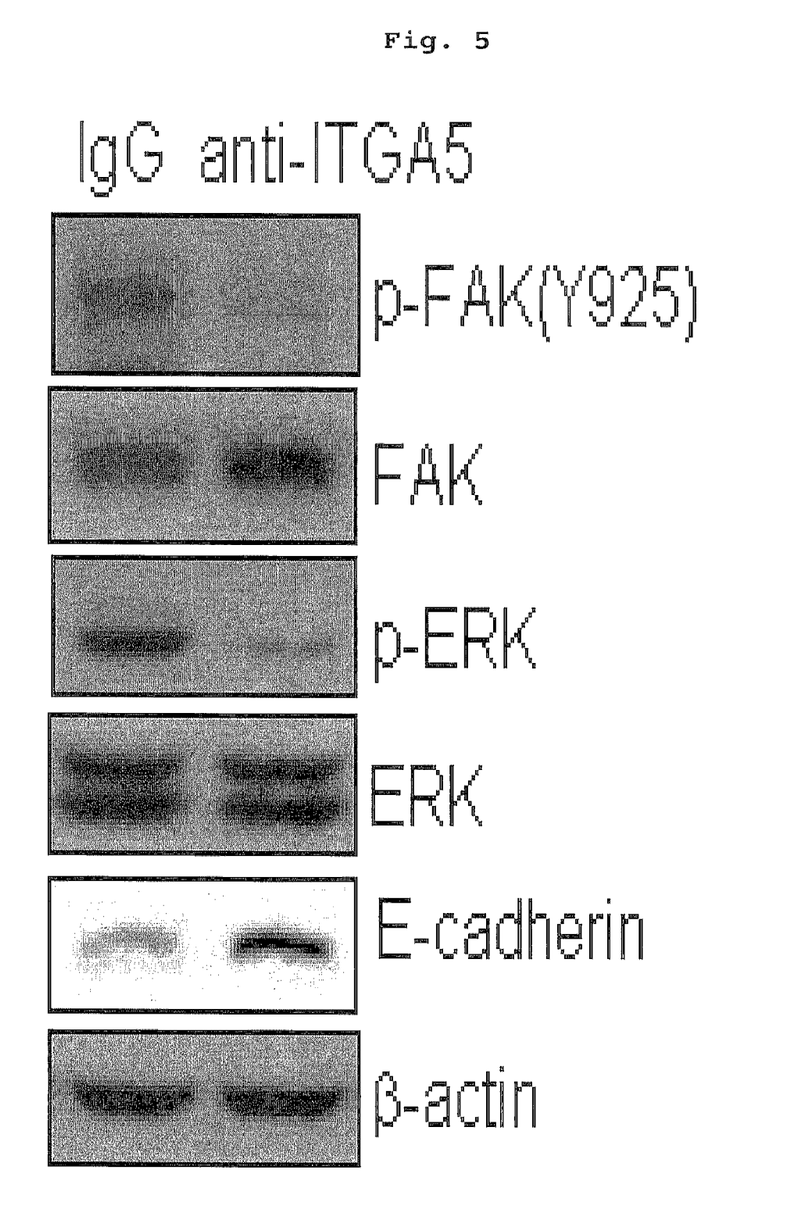
FIG. 5 is a diagram illustrating the results of Western blotting measuring the change of cell signal transduction and E-cadherin expression after inhibiting integrin alpha 5 activity using integrin alpha 5 specific anti-ITGA5.
Figure 6:
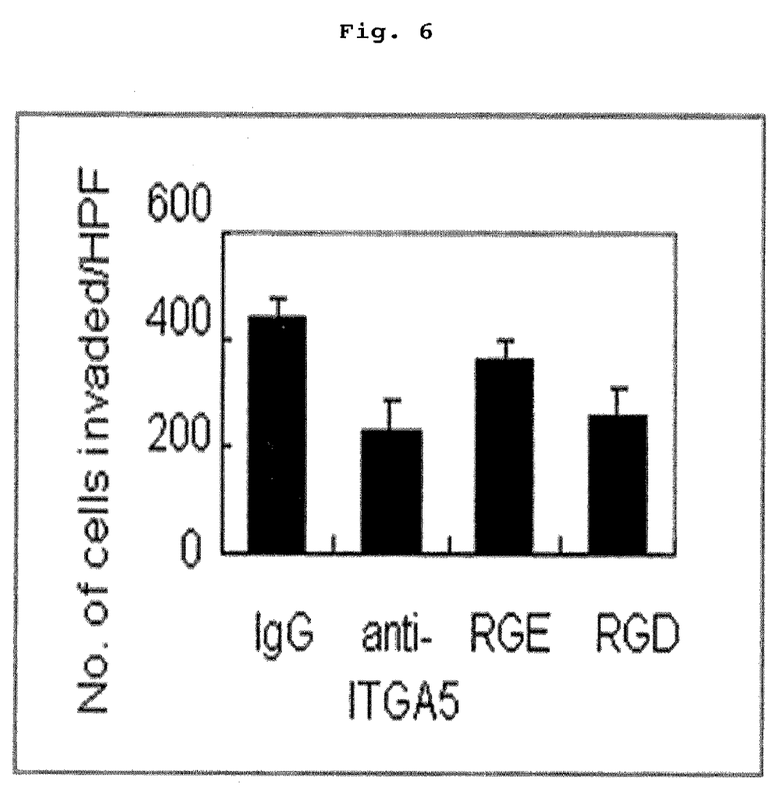
FIG. 6 is a graph illustrating the change of invaded cell number after inhibiting integrin alpha 5 activity using integrin alpha 5 specific anti-ITGA5 and RGD, in which IgG is the control and RGE peptide is the negative control.

To investigate the effect of integrin alpha 5 (ITGA5) inhibition, anti-ITGA5 was added to the cell line overexpressing SIP1/ZEB2. As a result, phosphorylation of ERK (extracellular signal-regulated kinase) and FAK (focal adhesion kinase) which are signal transferases was significantly reduced. In particular, inhibition of integrin alpha 5 activity resulted in the increase of E-cadherin expression (FIG. 5). Invasion was also investigated after adding anti-ITGA5 antibody. As a result, cancer cell invasion was reduced when anti-ITGA5 antibody or RGD peptide (integrin antagonist) was added, compared with when IgG (control) or RGE peptide (negative control) was added (FIG. 6).

Figure 7:
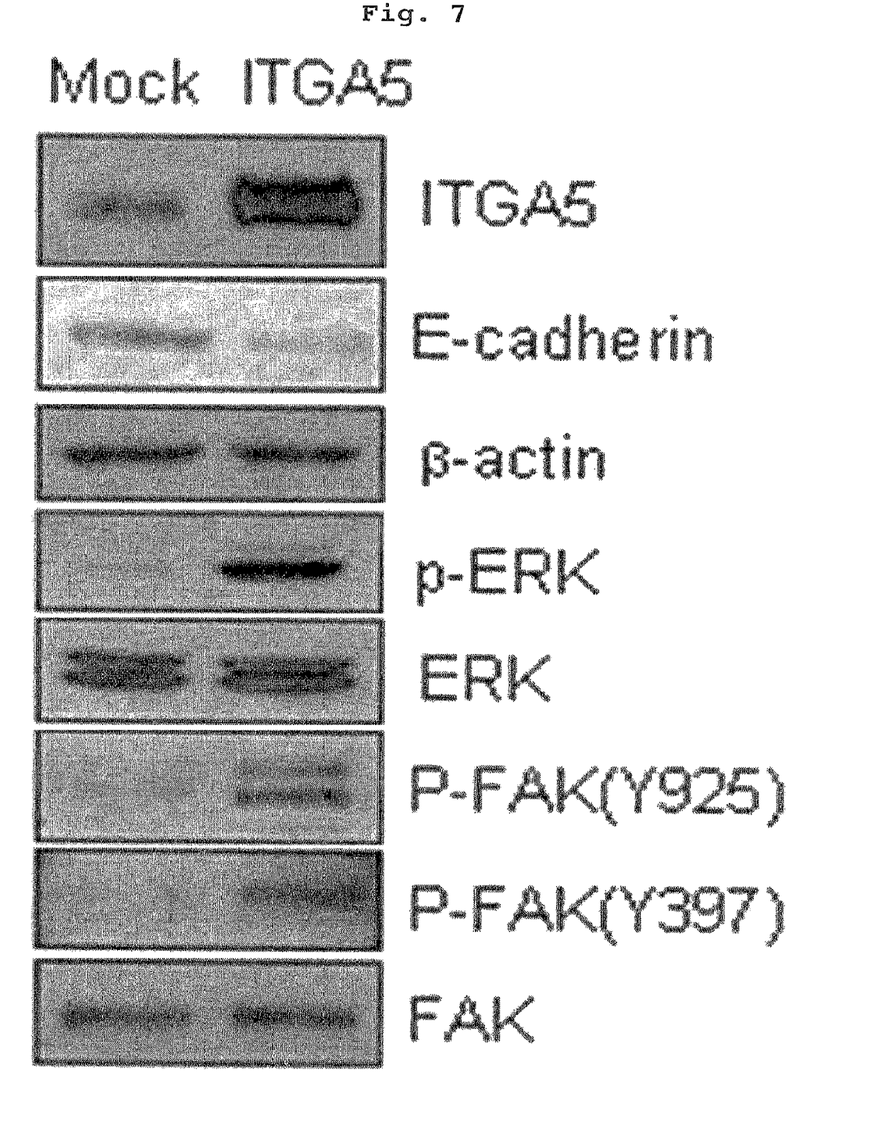
FIG. 7 is a diagram illustrating the results of Western blotting measuring the change of cell signal transduction and the expression levels of integrin alpha 5, E-cadherin and β-actin (control) after inserting integrin alpha 5.
Figure 8:
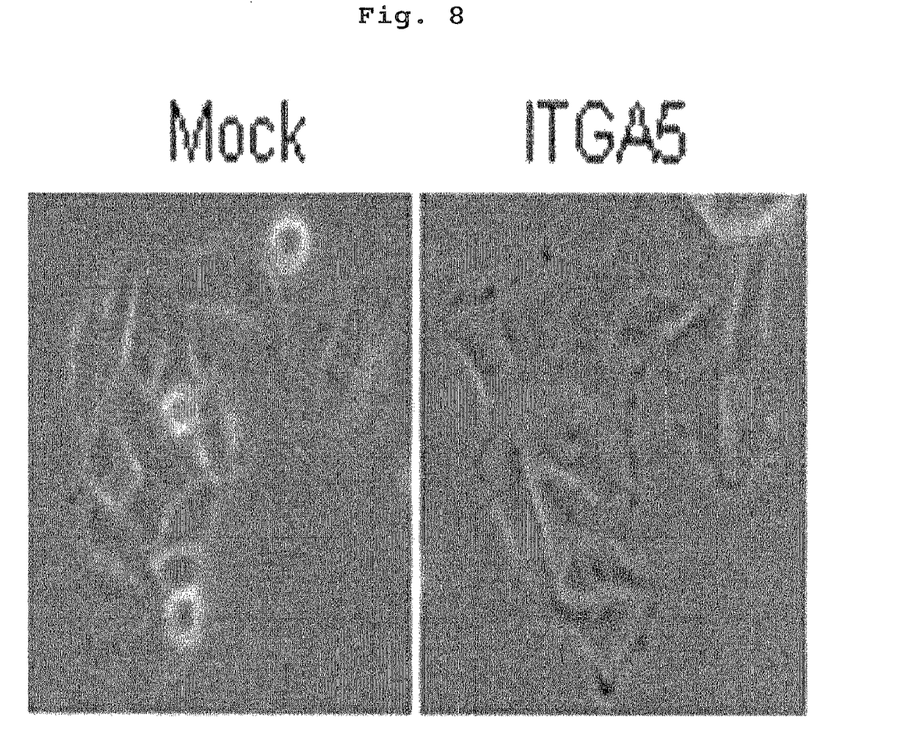
FIG. 8 is a set of photographs illustrating the cells inserted with integrin alpha 5 taken by optical microscope.
Figure 9:
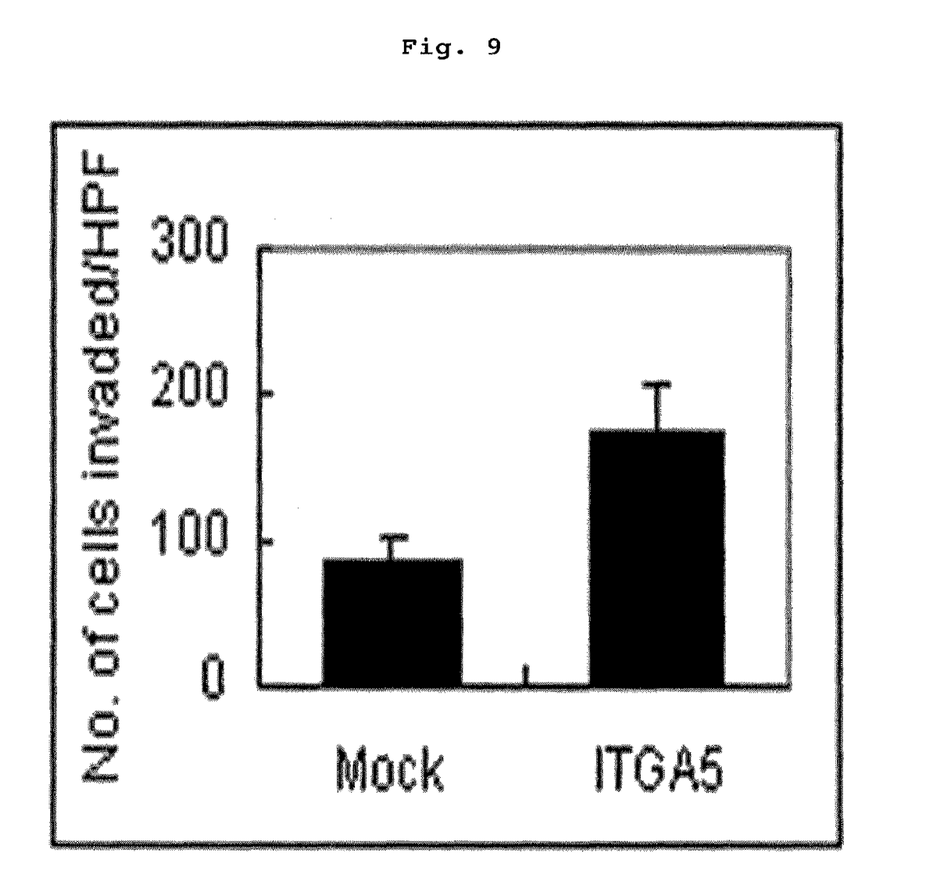
FIG. 9 is a graph illustrating the change of invaded cell number after the insertion of integrin alpha 5.

The effect of integrin alpha 5 (ITGA5) introduction was also investigated. Integrin alpha 5 (ITGA5) was introduced into the cell line that did not express SIP1/ZEB2. As integrin alpha 5 (ITGA5) was over-expressed, E-cadherin was down-regulated, but ERK and FAK phosphorylation was increased, which was consistent result in colon cancer cell line over-expressing SIP1/ZEB2 (FIG. 7). In the meantime, as integrin alpha 5 was over-expressed, cell spreading was increased and lamellipodium was formed (FIG. 8) and cancer cell invasion was increased (FIG. 9).

The above results indicate that over-expression of SIP1/ZEB2 results in the increase of integrin alpha 5 (ITGA5). Accordingly, phosphorylation of signal transferase increases but E-cadherin is down-regulated, leading to cancer cell invasion. So, once an integrin alpha 5 inhibitor is identified, it can be effectively used as anticancer agent or SIP1/ZEB2 inhibitor. Integrin alpha 5 expression reduced E-cadherin (FIG. 7), while integrin alpha 5 activity inhibition resulted in the increase of E-cadherin (FIG. 5), suggesting that integrin alpha 5 regulates the expression of E-cadherin in colon cancer cells. In conclusion, SIP1/ZEB2 induces integrin alpha 5 expression in colon cancer cells, resulting in invasion inhibition and E-cadherin down-regulation.

The present invention also provides a method for screening anticancer agent using fluorescent protein. The method comprises the following steps: 1) constructing an expression vector containing polynucleotide encoding fusion protein in which integrin alpha 5 (ITGA5) is conjugated with fluorescent protein; 2) transforming a cell line with the expression vector of step 1); 3) treating the transformed cell line of step 2) with sample compounds; 4) measuring fluorescence expressed in step 3) using fluorescent microscope; and 5) comparing the fluorescence of step 4) with that of the control to investigate whether it is reduced or not.

The fluorescent protein herein is preferably selected from the group consisting of green fluorescent protein (GFP), red fluorescent protein (RFP), blue fluorescent protein (BFP), yellow fluorescent protein (YFP), cyan fluorescent protein and enhanced green fluorescent protein (EGFP), but not always limited thereto. The cell line of step 2) is preferably SIP1/ZEB2 over-expressing cell line or SIP1/ZEB2 expression induced cell line. The SIP1/ZEB2 expression induced cell line is the one whose SIP1/ZEB2 expression is increased by the upstream target.

The present invention also provides a method for screening anticancer agent using a reporter gene. The method comprises the following steps: 1) constructing an expression vector containing a reporter gene operably linked to the promoter of integrin alpha 5 gene; 2) transforming a cell line with the expression vector of step 1); 3) treating the transformed cell line of step 2) with sample compounds; and 4) comparing the expression of the reporter gene in the cell line with that of the control to investigate whether it is reduced or not.

The reporter gene herein is preferably selected from the group consisting of chloramphenicol acetyl transferase (CAT) gene, beta-glucuronidase (GUS) gene, luciferase gene, beta-galactosidase gene, green fluorescent protein (GFP), red fluorescent protein (RFP), blue fluorescent protein (BFP), and yellow fluorescent protein (YFP), but not always limited thereto. The cell line of step 2) is preferably SIP1/ZEB2 over-expressing cell line or SIP1/ZEB2 expression induced cell line.

The method for screening anticancer agent of the present invention can be modified by those in the art, but it is understood that such modification is still within the spirit and scope of the present invention.

The present invention provides a composition for preventing and treating colon cancer comprising integrin alpha 5 (ITGA5) inhibitor as an active ingredient. In a preferred embodiment of the present invention, when integrin alpha 5 was inhibited, cell signal transduction was inhibited and cancer cell invasion was reduced (see Example 3). Therefore, it is expected that integrin alpha 5 inhibitor can be used for the prevention and treatment of colon cancer. The inhibitor preferably contains antisense nucleotide complementary to integrin alpha 5, siRNA (small interfering RNA), matrix analogue binding to integrin alpha 5 protein, antibody, and small compound inhibiting the protein activity, but not always limited thereto.

The present invention further provides a method for preventing and treating colon cancer containing the step of administering the composition comprising integrin alpha 5 inhibitor as an active ingredient to a subject.

The present invention also provides a composition for preventing and treating colon cancer comprising SIP1/ZEB2 inhibitor as an active ingredient. In a preferred embodiment of the present invention, when SIP1/ZEB2 was inhibited, integrin alpha 5 expression was decreased and cancer cell invasion was reduced (see Example 1). Therefore, it is expected that SIP1/ZEB2 inhibitor can be used for the prevention and treatment of colon cancer. The inhibitor preferably contains antisense nucleotide complementary to SIP1/ZEB2, siRNA (small interfering RNA), matrix analogue binding to SIP1/ZEB2 protein, antibody, and small compound inhibiting the protein activity, but not always limited thereto.

In addition, the present invention provides a method for preventing and treating colon cancer containing the step of administering the composition comprising SIP1/ZEB2 inhibitor as an active ingredient to a subject.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Effect of SIP1/ZEB2 Inhibition

To investigate the effect of SIP1/ZEB2 inhibition, SIP1/ZEB2-specific siRNA (small interfering RNA: referred as 'siRNA' hereinafter) was constructed, which was introduced into a cell line. The expression and invasion capacity were investigated.

<1-1> Construction of siRNA

To suppress the expression of SIP1/ZEB2, 4 kinds of synthetic siRNA dimer oligomers having the following sequences and non-specific siRNA (negative control) were purchased from Dharmacon (Chicago, Ill.). The said 4 different SIP1/ZEB2-specific siRNA sequences are as follows:

```
(1)
Sense sequence:
5'-GAACAGACAGGCUUACUUAUU-3'    (SEQ. ID. NO: 1)

Antisense sequence:
5'-UAAGUAAGCCUGUCUGUUCUU-3'    (SEQ. ID. NO: 2)

(2)
Sense sequence:
5'-GAAGCUACGUACUUUAAUAUU-3'    (SEQ. ID. NO: 3)

Antisense sequence:
5'-UAUUAAAGUACGUAGCUUCUU-3'    (SEQ. ID. NO: 4)

(3)
Sense sequence:
5'-CAACAUAUCCACUCCAUUUUU-3'    (SEQ. ID. NO: 5)

Antisense sequence:
5'-AAAUGGAGUGGAUAUGUUGUU-3'    (SEQ. ID. NO: 6)

(4)
Sense sequence:
5'-GGAGACAGAUCAGUAAUAUUU-3'    (SEQ. ID. NO: 7)

Antisense sequence:
5'-AUAUUACUGAUCUGUCUCCUU-3'    (SEQ. ID. NO: 8)
```

<1-2> Transformation

In the previous patent application (Korean Patent Publication No 20007-0114970) and the paper (Jung et al., Oncognen, 27:2645-2647, 2008) made by the present inventors, the said siRNA and non-specific siRNA were introduced in cells in which SIP1/ZEB2 expression was induced by over-expression of TMPRSS4, the upstream target of SIP1/ZEB2, by microporation technique (Incyto, Seoul, Korea). The introduction was performed according to the manufacturer's instructions. Briefly, cells were harvested, washed with PBS, and resuspended in R buffer at the density of $3 \times 10^5$ cell/12 µL. 2 µL of 20 µM siRNA was added thereto, followed by transformation using microporator.

<1-3> Investigation of SIP1/ZEB2 Expression after Inhibiting SIP1/ZEB2

SIP1/ZEB2 expression level was investigated by RT-PCR. Particularly, total RNA was extracted from the cell line of Example <1-2> using high pure RNA isolation kit (Roche, Mannheim, Germany). The extracted RNA (5 µg) was denatured at 70° C. for 10 minutes, followed by reverse transcription with oligo(dT) primer using SuperScript II reverse transcriptase (Invitrogen) at 42° C. for 1 hour. The reverse transcriptase was inactivated at 90° C. for 2 minutes. The synthesized cDNA was amplified by PCR with the forward primer represented by SEQ. ID. NO: 9 (5'-TCTCGCCCGAGTGAAGCCTT-3') and the reverse primer represented by SEQ. ID. NO: 10 (5'-GGGAGAATTGCTTGATGGAGC-3'). In the meantime, β-actin was used as the internal control. As β-actin specific primers, the forward primer represented by SEQ. ID. NO: 11 (5'-GCTCGTCGTCGACAACGGCTC-3') and the reverse primer represented by SEQ. ID. NO: 12 (5'-CAAACATGATCTGGGTCATCTTCTC-3') were used.

PCR was performed as follows; predenaturation at 94° C. for 2 minutes, denaturation at 94° C. for 30 seconds, annealing at 58° C. (55° C. for β-actin) for 30 seconds, polymerization at 72° C. for 2 minutes, 30 cycles from denaturation to polymerization, and final extension at 72° C. for 10 minutes. The PCR product was electrophoresed on 2% agarose gel or 8% polyacrylamide gel. All the reactions were repeated at least two times.

The results of investigation of SIP1/ZEB2 expression are shown in the upper part of FIG. 1. As shown in FIG. 1, when SIP1/ZEB2 specific siRNA was introduced, SIP1/ZEB2 expression was significantly reduced, compared with that of the negative control. Therefore, it was confirmed that SIP1/ZEB2 specific siRNA could inhibit SIP1/ZEB2 effectively.

<1-4> Investigation of Integrin Alpha 5 (ITGA5) Expression after Inhibiting SIP1/ZEB2

Western blotting was performed to investigate integrin alpha 5 (ITGA5) expression according to the inhibition of SIP1/ZEB2 as follows: Cells were lysed in RIPA buffer (10 mM Tris, pH7.2, 150 mM NaCl, 1% deoxycholate, 1% Triton X-100, 0.1% SDS, 1 mM sodium orthovanadate, 50 mM NaF, 1 mM PMSF, complete protease inhibitor). The cell lysate was quantified by modified Bradford assay (Bio-Rad Laboratories, Hercules, Calif.) on the market. 30 µg of the cell lysate was mixed with SDS sample buffer, followed by heating. Electrophoresis was performed on 6 or 10% SDS-PAGE gel. Isolated protein was transferred onto nitrocellulose membrane, followed by blocking with 5% skim milk. Then anti-beta-actin (1:1000, Santa Cruz) and anti-ITGA5 (1:1000, BD transduction laboratories) were added thereto and later horseradish peroxidase conjugated secondary antibody was added for reaction. ECL kit (ECL Plus, Amersham, USA) was treated according to the manufacturer's instructions.

As a result, as shown in the bottom of FIG. 1, when SIP1/ZEB2 specific siRNA was introduced, integrin alpha 5 (ITGA5) expression was significantly reduced, compared with the negative control introduced with non-specific siRNA. Therefore, it was confirmed that SIP1/ZEB2 was closely related to integrin alpha 5 expression.

<1-5> Cancer Cell Invasion According to the Inhibition of SIP1/ZEB2

To investigate cancer cell invasion according to the inhibition of SIP1/ZEB2, invasion assay was performed with the cell lines respectively treated with specific siRNA and non specific siRNA of Example <1-2>. Particularly, 24-well transwell plate (8 μm pore size; Costar, Corning, USA) was coated with 100 μl of matrigel (BD Biosciences, Bedford, USA) diluted with serum free medium at the concentration of 250 μg/ml, followed by fixation at room temperature for 1 hour. Lower chamber of the transwell plate was coated with 100 μl of human collagen type I (10 μg/ml, Chemicon, TemecuLa, USA) as a chemoattractant. $2.5 \times 10^4$ cells cultured in serum free medium were distributed on upper chamber, followed by culture in a 37° C., 5% $CO_2$ incubator for 48 hours, during which migration from upper chamber to lower chamber was induced. Cells not transferred were eliminated from the surface of upper chamber. Cells moved to lower chamber were fixed with 3.7% paraformaldehyde dissolved in PBS, followed by staining with 2% crystal violet solution. Remaining crystal violet solution was washed with distilled water. Selected area (×200) was photographed. Migrated cells in 3 selected areas (×200) were calculated. Experiments were repeated at least twice with two selected areas under the same conditions and the representative one was presented. Data reflects migrated cells±standard deviation.

As a result, as shown in FIG. 2, when SIP1/ZEB2 expression was inhibited, number of cancer cells that decomposed matrigel and moved was reduced 35% by that of the control. The above result indicates that SIP1/ZEB2 plays a key role in cancer cell invasion and metastasis.

Example 2

Investigation of the Effect of SIP1/ZEB2 Introduction

To investigate the effect of SIP1/ZEB2 introduction, SIP1/ZEB2 expression construct was prepared, with which colon cancer cells were transformed. Then, Integrin alpha 5 expression and cancer cell invasion according to SIP1/ZEB2 over-expression were investigated.

<2-1> Preparation of Animal Cell Expression Construct

SIP1/ZEB2 coding cDNA was provided by Mammalian Gene Collection (NIH, USA). The cDNA was amplified by PCR using Pfu polymerase (Stratagene), followed by subcloning into pcDNA3.1 (Invitrogen). To increase purification efficiency, myc tag was added to N-terminal of SIP1/ZEB2.

For the PCR, the forward primer represented by SEQ. ID. NO: 13 (5'-GCTCTAGA GAG CAG AAA CTC ATC TCT GAA GAG GAT CTG atgaagcagc cgatcatggc-3') and the reverse primer represented by SEQ. ID. NO: 14 (5'-GCTCTAGA ttaca tgccatcttc catat-3') were used.

PCR was performed using SIP1/ZEB2 cDNA as a template as follows: predenaturation at 94° C. for 4 minutes, denaturation at 94° C. for 30 seconds, annealing at 58° C. for 30 seconds, polymerization at 72° C. for 4 minutes, 25 cycles from denaturation to polymerization, and final extension at 72° C. for 10 minutes. The PCR product and pcDNA3.1 were digested with XbaI, followed by purification. 100 ng of vector and 100 ng of insert were mixed with 1 unit of ligase (Roche), followed by reaction at 16° C. for 16 hours. After ligation, *E. coli* XL1-Blue (Stratagene, USA) was transformed, followed by selection in the plate containing ampicillin. Plasmid containing wanted DNA fragment was obtained by digesting with proper restriction enzymes. DNA sequencing was performed to confirm the plasmid. The constructed expression vector was named 'pcDNA3.1-myc-SIP1/ZEB2'.

<2-2> Transformation

SW480 cells were transformed with the expression vector constructed in Example <2-1> and empty vector (control) that did not contain SIP1/ZEB2 by microporation technique.

<2-3> Integrin Alpha 5 Expression Pattern According to SIP1/ZEB2 Over-Expression The cells transformed in Example <2-2> were lysed three days after the transformation. Western blotting was performed with the cell lysate by the same manner as described in Example <1-4> to confirm SIP1/ZEB2 over-expression and to investigate integrin alpha 5 expression pattern. Beta-actin was used as the internal control. SIP1/ZEB2 expression was measured by using anti-myc antibody (1:1000, Upstate), integrin alpha 5 expression was measured by using anti-ITGA5 antibody (1:1000, BD transduction laboratories), and beta-actin expression was measured by using anti-beta actin antibody (1:1000, Santa Cruz). In addition, anti-pY925FAK (1:1000, Cell signaling technology), anti-pY397FAK (1:1000, Santa Cruz), anti-FAK (1:1000, Santa Cruz), anti-pERK (1:1000, Cell signaling technology), anti-ERK (1:1000, Cell signal), and anti-E-cadherin (1:1000, R&D systems) were used for the analysis performed by the same manner as describe in Example <1-4>.

As shown in FIG. 3, SIP1/ZEB2 was over-expressed in the cells transformed with SIP1/ZEB2 expression vector, compared with the control cells transformed with mock vector, suggesting that the expression vector was successfully introduced. It was also confirmed that integrin alpha 5 (ITGA5) was up-regulated by SIP1/ZEB2 over-expression. Therefore, it is believed that SIP1/ZEB2 induces integrin alpha 5. In addition, over-expression of SIP1/ZEB2 resulted in the decrease of E-cadherin but the increase of ERK and FAK phosphorylation. This result indicates that SIP1/ZEB2 induces major signal transduction in relation to invasion in colon cancer cells.

<2-4> Investigation of Cancer Cell Invasion According to SIP1/ZEB2 Over-Expression To investigate cancer cell invasion according to SIP1/ZEB2 over-expression, invasion assay was performed by the same manner as described in Example <1-5>.

As a result, as shown in FIG. 4, cancer cell invasion was significantly increased by SIP1/ZEB2 introduction.

Therefore, it was confirmed that SIP1/ZEB2 played an important role in cancer cell invasion and metastasis.

Example 3

Effect by Integrin Alpha 5 (ITGA5) Inhibition

<3-1> Changes of Cell Signal Transduction According to Integrin Alpha 5 Inhibition To investigate changes of cell signal transduction according to integrin alpha 5 inhibition, integrin alpha 5 expression was suppressed by using anti-ITGA5 antibody (BD transduction lab. Cat. No 555614) functioning as the antagonist, followed by measurement of phosphorylation levels of FAK (focal adhesion kinase) and ERK (extracellular signal-regulated kinase). Normal IgG was used for the control.

Particularly, the SIP1/ZEB2 over-expressing cell line, prepared in Example <1-3>, was harvested. $7 \times 10^5$ cells were mixed with 25 μg/mL of anti-ITGA5 antibody (BD transduction lab. Cat. No 555614) functioning as the antagonist and IgG, followed by pre-culture at 37° C. for 20 minutes.

The cells were smeared in a 6-well plate. 10 hours later, the cells were lysed and Western blotting was performed with the obtained cell lysate by the same manner as described in Example <1-4>. At this time, anti-pY925FAK antibody (1:1000, Cell signaling technology), anti-FAK (1:1000, Santa Cruz), anti-pERK (1:1000, Cell signaling technology), anti-ERK (1:1000, Cell signal) and anti-E-cadherin (1:1000, R&D systems) were used to measure phosphorylation levels of FAK and ERK, and expression level of E-cadherin.

As shown in FIG. 5, it was confirmed from the Western blotting that when integrin alpha 5 expression was inhibited by anti-ITGA5 antibody, phosphorylation levels of FAK and ERK were significantly reduced, compared with the control treated with normal IgG. In the meantime, E-cadherin expression was increased. In conclusion, integrin alpha 5 inhibition results in the decrease of cell signal transduction, suggesting that integrin alpha 5 inhibition can suppress metastasis.

<3-2> Investigation of Cancer Cell Invasion According to Integrin Alpha 5 Inhibition To investigate cancer cell invasion according to integrin alpha 5 inhibition, integrin alpha 5 expression was inhibited by using anti-ITGA5 antibody and RGD, the peptide inhibitor, followed by invasion assay by the same manner as described in Example <1-5>.

As an integrin alpha 5 expression inhibitor, RGD peptide, the well-known antagonist of integrin including 1) anti-ITGA5 and 2) integrin alpha 5 beta 1, was used. IgG was used as the control and RGE peptide was used as the negative control. The peptide was synthesized in Peptron (Korea).

As shown in FIG. 6, when integrin alpha 5 was inhibited by anti-ITGA5 antibody and RGD peptide, cancer cell invasion was significantly reduced, compared with the control treated with IgG and the negative control treated with RGE. The above result indicates that integrin alpha 5 plays a key role in cancer cell invasion and metastasis.

Example 4

Effect of Integrin Alpha 5 Introduction

To investigate the effect of integrin alpha 5 introduction, integrin alpha 5 expression construct was prepared, with which colon cancer cells were transformed. Then, changes of cell signal transduction and cancer cell invasion according to integrin alpha 5 over-expression were investigated.

<4-1> Preparation of Animal Cell Expression Construct

Integrin alpha 5 coding cDNA was provided by Seoul National University (Korea). The cDNA was amplified by PCR using Pfu polymerase (Stratagene), followed by subcloning into pcDNA3.1 (Invitrogen).

For the PCR, the forward primer represented by SEQ. ID. NO: 15 (5'-<u>GCTCTAGA</u>atggggagccgg acgccag-3') and the reverse primer represented by SEQ. ID. NO: 16 (5'-<u>GCTCTAGA</u>tcaggcatcagaggtggc-3') were used. PCR was performed using integrin alpha 5 cDNA as a template as follows: predenaturation at 94° C. for 4 minutes, denaturation at 94° C. for 30 seconds, annealing at 55° C. for 30 seconds, polymerization at 72° C. for 4 minutes, 25 cycles from denaturation to polymerization, and final extension at 72° C. for 10 minutes. The PCR product and pcDNA3.1 were digested with XbaI, followed by purification. 100 ng of vector and 100 ng of insert were mixed with 1 unit of ligase (Roche), followed by reaction at 16° C. for 16 hours. After ligation, *E. coli* XL1-Blue (Stratagene, USA) was transformed, followed by selection in the plate containing ampicillin. Plasmid containing wanted DNA fragment was obtained by digesting with proper restriction enzymes. DNA sequencing was performed to confirm the plasmid. The constructed expression vector was named 'pcDNA3.1-ITGA5'.

<4-2> Transformation

SW480 cells were transformed with the expression vector constructed in Example <4-1> and empty vector (control) that did not contain ITGA5 by microporation technique.

<4-3> Changes of Integrin Alpha 5 Expression and Cell Signal Transduction According to Integrin Alpha 5 Over-Expression The cells transformed in Example <4-2> were lysed three days after the transformation. Western blotting was performed with the cell lysate by the same manner as described in Example <1-4> to confirm integrin alpha 5 over-expression and to investigate changes of cell signal transduction. Beta-actin was used as the internal control. Integrin alpha 5 expression was measured by using anti-ITGA5 (1:1000, BD transduction laboratories), and beta-actin expression was measured by using anti-beta actin antibody (1:1000, Santa Cruz). In addition, anti-pY925FAK (1:1000, Cell signaling technology), anti-pY397FAK (1:1000, Santa Cruz), anti-FAK (1:1000, Santa Cruz), anti-pERK (1:1000, Cell signaling technology), anti-ERK (1:1000, Cell signal), and anti-E-cadherin (1:1000, R&D systems) were used for the analysis performed by the same manner as describe in Example <1-4>.

As shown in FIG. 7, integrin alpha 5 was over-expressed in the cells transformed with integrin alpha 5 expression vector, compared with the control cells transformed with mock vector, suggesting that the expression vector was successfully introduced. In addition, over-expression of integrin alpha 5 resulted in the decrease of E-cadherin but the increase of ERK and FAK phosphorylation. This result indicates that integrin alpha 5 directly mediates signal transduction/invasion. In particular, integrin alpha 5 reduced E-cadherin (FIG. 7), while integrin alpha 5 inhibition increased E-cadherin (FIG. 5), suggesting that E-cadherin expression in colon cancer cells is regulated by integrin alpha 5.

<4-4> Changes of Cell Morphology According to Integrin Alpha 5 Over-Expression

Cell morphology was observed in those cells transformed with integrin alpha 5 expression vector and mock vector in Example <4-2> under optical microscope (×100, Nikon light microscope). As a result, as shown in FIG. 8, cell spreading was increased and lamellipodium was formed by integrin alpha 5.

<4-5> Investigation of Cancer Cell Invasion According to Integrin Alpha 5 Over-Expression To investigate cancer cell invasion according to integrin alpha 5 over-expression, invasion assay was performed by the same manner as described in Example <1-5>.

As a result, as shown in FIG. 9, cancer cell invasion was significantly increased by integrin alpha 5 over-expression, compared with when the mock vector was introduced.

Therefore, it was confirmed that integrin alpha 5 played an important role in cancer cell invasion and metastasis.

Invasion of colon cancer cells transformed respectively with SIP1/ZEB expression vector and integrin alpha 5 expression vector was measured and presented as a ratio to that of the control cells transformed with mock vector based on the results of FIG. 4 and FIG. 9. From the results of FIG. 3 and FIG. 7, expression level of integrin alpha 5 was quantified by densitometry. The expression level was normalized by using expression level of beta-actin and then integrin alpha 5 expression of each case was calculated.

Figure 10:
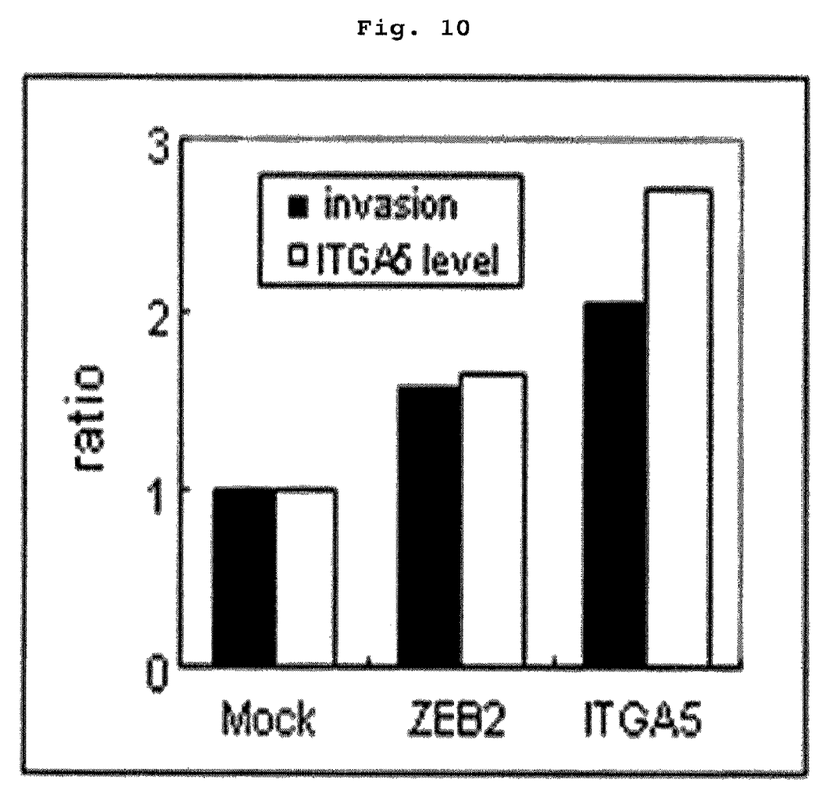
FIG. 10 is a graph illustrating the invasion ratio of SPI1/ZEB2 and integrin alpha 5 to those of cells transfected with empty vector (FIG. 4 and FIG. 9) and expression ratio of integrin alpha 5 (FIG. 3 and FIG. 7).

As shown in FIG. 10, invasion of colon cancer cells transformed with SIP1/ZEB2 expression vector or integrin alpha 5 expression vector was increased, compared with that of the cells transformed with mock vector (control), and the invasion capacity was increased in proportion to the integrin alpha 5 expression level.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for identifying an anti-invasion or anti-metastasis agent comprising the following steps:
   1) contacting a cell line that over-expresses SIP1/ZEB2 with a sample compound; and
   2) determining the expression of integrin alpha 5 (ITGA5) in the cell line in the presence and absence of the sample compound,
   wherein reduction of ITGA5 expression in the cell line in the presence of the sample compound relative to the absence of the sample compound identifies the sample compound as an anti-invasion or anti-metastasis agent.

2. The method of claim 1, wherein the cell line that over-expresses SIP1/ZEB2 comprises an expression vector comprising a reporter gene operably linked to the promoter of the ITGA5 gene.

3. The method of claim 2, wherein the reporter gene is selected from the group consisting of chloramphenicol acetyl transferase (CAT) gene, beta-glucuronidase (GUS) gene, luciferase gene, beta-galactosidase gene, green fluorescent protein (GFP), red fluorescent protein (RFP), blue fluorescent protein (BFP), and yellow fluorescent protein (YFP).

4. The method of claim 1, wherein the cell line that over-expresses SIP1/ZEB2 comprises an expression vector comprising a polynucleotide encoding a fusion protein of ITGA5 conjugated to a fluorescent protein.

5. The method of claim 1, wherein the cell line that over-expresses SIP1/ZEB2 comprises an expression vector comprising a polynucleotide encoding SIP1/ZEB2.

6. The method of claim 1, wherein the cell line is a colon cancer cell line.

* * * * *